United States Patent
Perry et al.

(10) Patent No.: US 6,322,777 B1
(45) Date of Patent: Nov. 27, 2001

(54) FRAGRANCE RELEASING NON-VOLATILE POLYMERIC SILOXANES

(75) Inventors: Robert J. Perry, Niskayuna; John A. Kilgour, Clifton Park, both of NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/420,715

(22) Filed: Oct. 20, 1999

Related U.S. Application Data

(62) Division of application No. 09/143,641, filed on Aug. 28, 1998, now Pat. No. 6,054,577.

(51) Int. Cl.$^7$ ...................................................... A61K 7/32
(52) U.S. Cl. ........................ 424/65; 424/70.12; 424/76.1; 424/78.02; 514/63; 512/1; 512/25
(58) Field of Search ..................... 424/65, 70.12, 424/76.1, 78.02; 514/63; 512/1, 25

(56) References Cited

U.S. PATENT DOCUMENTS

| | | |
|---|---|---|
| 2,679,496 | 5/1954 | Bunnell . |
| 3,271,305 | 9/1966 | Allen et al. . |
| 3,779,987 | 12/1973 | Razzano . |
| 4,445,641 | 5/1984 | Baker et al. . |
| 4,500,725 | 2/1985 | Yemoto et al. . |
| 4,524,018 | 6/1985 | Yemoto et al. . |
| 4,908,208 | 3/1990 | Lee et al. . |
| 5,008,115 | 4/1991 | Lee et al. . |
| 5,071,704 | 12/1991 | Fischel-Ghodsian . |
| 5,130,171 | 7/1992 | Prud'Homme et al. . |
| 5,160,494 | 11/1992 | Krzysik et al. . |
| 5,176,903 | 1/1993 | Goldberg et al. . |
| 5,185,155 | 2/1993 | Behan et al. . |
| 5,234,689 | 8/1993 | Lindauer et al. . |
| 5,324,444 | 6/1994 | Berry et al. . |
| 5,372,806 | 12/1994 | Holloway . |
| 5,387,411 | 2/1995 | Abrutyn et al. . |
| 5,387,622 | 2/1995 | Yamamoto . |
| 5,449,512 | 9/1995 | Simmons . |
| 5,490,982 | 2/1996 | Siciliano . |
| 5,500,223 | 3/1996 | Behan et al. . |
| 5,508,259 | 4/1996 | Holzner et al. . |
| 5,525,555 | 6/1996 | Zank . |
| 5,525,588 | 6/1996 | Michetti . |
| 6,054,547 | * 4/2000 | Perry et al. ........................ 424/65 X |

FOREIGN PATENT DOCUMENTS

| | | |
|---|---|---|
| 2041964 A | 9/1980 | (GB) . |
| WO 96/28497 | 9/1996 | (WO) . |
| WO 9628497 A | 9/1996 | (WO) . |

* cited by examiner

*Primary Examiner*—Paul F. Shaver
(74) *Attorney, Agent, or Firm*—Kenneth S. Wheelock

(57) ABSTRACT

A fragrance releasing siloxane comprising a substituent having the formula $(R^1O)_a(R^2O)_b(R^3O)_c(R^4O)_d(R^5O)_e SiR^U$ with $R^U$ a two to forty atom divalent hydrocarbon radical where $R^1O$, $R^2O$ and $R^3O$ are each independently fragrant alkoxide moieties, derived from the alcohols $R^1OH$, $R^2OH$ and $R^3OH$ wherein $R^1OH$, $R^2OH$ and $R^3OH$ are independently fragrant alcohols with $R^4$ and $R^5$ selected from the group consisting of monovalent hydrocarbon radicals having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that $a+b+c+d+e=3$.

10 Claims, No Drawings

FRAGRANCE RELEASING NON-VOLATILE POLYMERIC SILOXANES

CROSS-REFERENCE TO RELATED APPLICATIONS

This a divisional of application Ser. No. 09/143,641 filed on Aug. 28, 1998 now U.S. Pat. 6,054,577.

STATEMENT REGARDING FEDERALLY FUNDED RESEARCH

Not Applicable

FIELD OF THE INVENTION

The present invention relates to non-volatile oligomeric or polymeric siloxanes which may be linear, branched or cross-linked, suitable for use in a variety of applications including personal care formulations, house-hold products, automotive, textiles and molding materials wherein the non-volatile polymeric siloxane has been chemically modified to release a fragrant molecule upon hydrolysis. The present invention further relates to such molecules where the rate of fragrant molecule release is sufficiently slow so that products formulated with the modified polymeric non-volatile siloxane exhibit a desirable fragrance for long periods of time.

BACKGROUND OF THE INVENTION

The slow sustained release of a fragrant molecule is a highly desirable trait in many personal care products. A number of means have been proposed and implemented to achieve this goal. Among these means are dissolving or suspending fragrant compounds in personal care emulsions (U.S. Pat. Nos. 5,525,588; 5,525,555; 5,490,982; and 5,372, 806), encapsulation of a fragrant compound (U.S. Pat. Nos. 5,500,223; 5,324,444; 5,185,155; 5,176,903; and 5,130, 171), dissolving a fragrant compound into a hydrophobic phase such as a silicone (U.S. Pat. Nos. 5,449,512; 5,160, 494 and 5,234,689), incorporation of a fragrant compound into cross-linked polymers (U.S. Pat. Nos. 5,387,622 and 5,387,411), incorporation of fragrant compounds into permeable laminates (U.S. Pat. Nos. 5,071,704 and 5,008,115), incorporation of fragrant compounds into matrices that soften at body temperature (U.S. Pat. No. 4,908,208), incorporation of fragrant compounds into rate controlling membranes (U.S. Pat. No. 4,445,641) and derivatization of silanes with fragrant alcohols to form alkoxy silanes (U.S. Pat. Nos. 4,524,018 and 4,500,725). All of these approaches suffer from one or more of the following problems: 1) the material is not stable in a personal care formulation, 2) the material is not easy or convenient to prepare, or 3) the material does not release the fragrant compound in a slow and sustained fashion.

SUMMARY OF THE INVENTION

The present invention provides for A fragrance releasing siloxane having the formula:

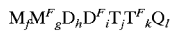

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7, R^8, R^9, R^{10}, R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1O)_a(R^2O)_b(R^3O)_c(R^4)_d(R^5)_eSiR^U$ with $R^U$ a two to forty atom divalent hydrocarbon radical where $R^1O$, $R^2O$ and $R^3O$ are each independently fragrant alkoxide moieties, derived from the alcohols $R^1OH$, $R^2OH$ and $R^3OH$ wherein $R^1OH$, $R^2OH$ and $R^3OH$ are independently fragrant alcohols with $R^4$ and $R^5$ selected from the group consisting of monovalent hydrocarbon radicals having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3. The present invention also provides for compositions that comprise a fragrance releasing siloxane. Of particular use are cosmetic compositions that comprise a fragrance releasing siloxane.

DETAILED DESCRIPTION OF THE INVENTION

The compounds of the present invention introduce fragrant moieties via hydrosilylation of an olefinic silane molecule. These siloxane molecules are useful in a variety of personal care compositions. The present invention is directed to new compositions of matter that are siloxanes that release a fragrant alcohol upon hydrolysis.

The olefinic silanes utilized by the present invention are described by the formula:

where $R^1O$, $R^2O$ and $R^3O$, fragrant alkoxide moieties, are selected (or derived from) from the group of alcohols consisting of $R^1OH$, $R^2OH$ and $R^3OH$ wherein $R^1OH$, $R^2OH$ and $R^3OH$ are fragrant alcohols with $R^4$ and $R^5$ selected from the group consisting of monovalent hydrocarbon radicals having from one to forty carbon atoms and monovalent alkoxy radicals having from one to forty carbon atoms, $R^6$ a two to forty atom monovalent unsaturated hydrocarbon radical containing a-terminal olefinic or acetylenic moiety where the subscript a has a value ranging from 1 to 3 and the subscripts b, c, d, and e have values ranging from 0 to 2 subject to the limitation that a+b+c+d+e=3. =3. As used herein, the phrase monovalent hydrocarbon radical includes both aliphatic and aromatic monovalent hydrocarbon radicals that may also include hetero-atoms such as oxygen, nitrogen, sulfur and the halogens, fluorine, chlorine, bromine and iodine.

The following synthetic examples are intended to illustrate the general synthetic reactions schemes that a person having ordinary skill in the art of silicones chemistry would typically employ in order to prepare the olefinic silanes used by the present invention. These reaction schemes are thus illustrative only and do not represent the only synthetic pathways that may be utilized.

When the starting material is a fragrant alcohol such as phenethanol, olefinic halosilanes or olefinic silicon alkoxides may be employed as starting materials to produce the fragrance-releasing siloxanes of the present invention via fragrance bearing olefinic silanes.

Reaction scheme I

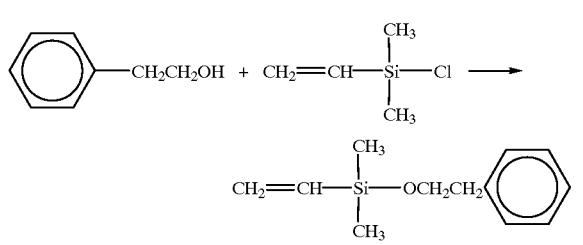

Reaction scheme II

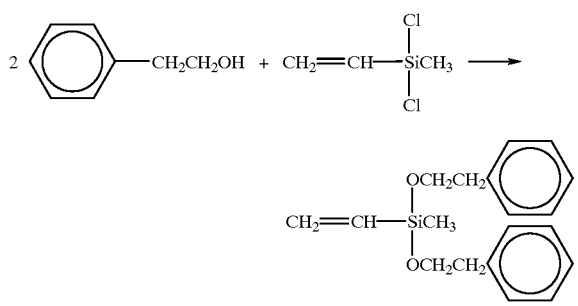

Reaction scheme III

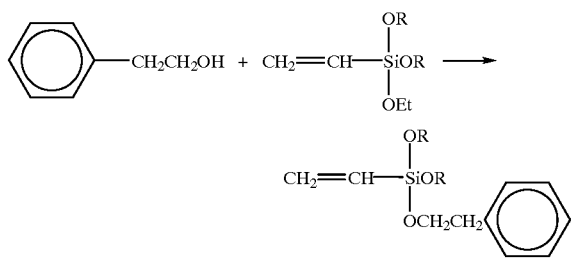

Where the R groups for reaction III may be Et (C$_2$H$_5$—) or —CH$_2$CH$_2$C$_6$H$_5$. Similarly 3-methyl-5-(2,2,3,-trimethyl-3-cyclopenten-1-yl)-4-penten-2-ol will react with chloromethylvinylsilane in a similar fashion, reaction scheme IV:

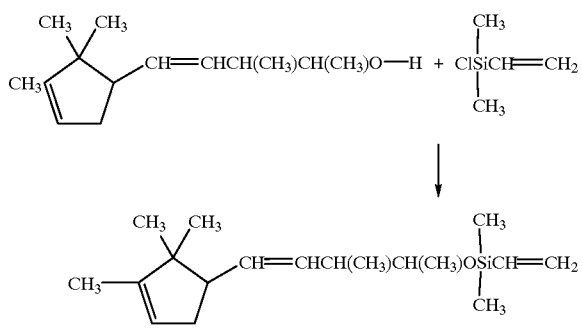

as will allyldimethylchlorosilane react with citronellol in a similar, reaction scheme V:

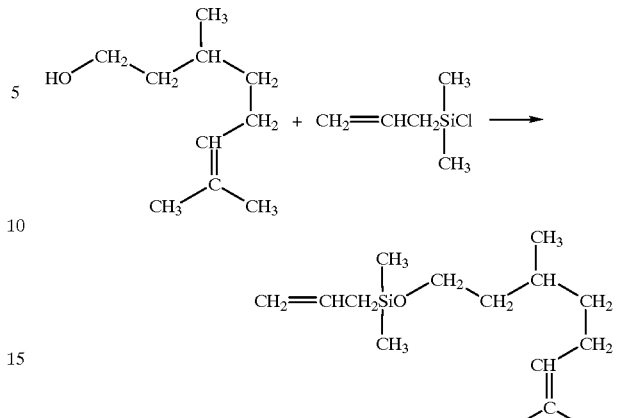

The fragrant alcohols that are precursors of the silanes of the present invention are selected from the group consisting of 3-methyl-5-(2,2,3,-trimethyl-3-cyclopenten-1-yl)-4-penten-2-ol, 2-methylbutanol, 3-pentanol, n-pentanol, 2-pentanol, n-hexanol, 2-methylpentanol, 1-decanol, sandela, nonadyl, dimetol, thymol, 1-heptanol, menthol, eugenol, vanillan, o-vanillan, 4-(P-hydroxyphenyl)-2-butanone, syringealdehyde, prenol, cis-3-hexanol, trans-3-hexanol, cis-4-heptenol, trans-2-octenol, trans-2-cis-6-nonadienol, geraniol, nerol, citronellol, crotyl alcohol, oleyl alcohol, linalool, α-terpineol, β-phenethyl alcohol, cinnamic alcohol, benzyl alcohol, α-methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octen-ol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool and 2-phenoxyethanol.

The fragrance releasing siloxanes of the present invention are prepared from an organohydrogen siloxane via conventional hydrosilylation using the fragrance bearing olefinic silane as the alkenyl source. Thus an organohydrogensiloxane having the formula:

$$M_f M^H_g D_h D^H_i T_j T^H_k Q_l$$

where M has the formula $R^7R^8R^9SiO_{1/2}$; $M^H$ has the formula $R^7R^8HSiO_{1/2}$; D has the formula $R^{10}R^{11}SiO_{2/2}$; $D^H$ has the formula $R^{10}HSiO_{2/2}$; T has the formula $R^{12}SiO_{3/2}$; $T^H$ has the formula $HSiO_{3/2}$; and Q has the formula $SiO_{4/2}$ where $R^7$, $R^8$, $R^9$, $R^{10}$, $R^{11}$ and $R^{12}$ are each independently selected for each M, $M^H$, D, $D^H$, and T from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one.

The organohydrogensiloxane is reacted under hydrosilylation conditions to produce a fragrance releasing siloxane having the formula:

$$M_f M^F_g D_h D^F_i T_j T^F_k Q_l$$

where the components and subscripts satisfy the previous definitions and requirements and $M^F$ has the formula $R^7R^8R^FSiO_{1/2}$; $D^F$ has the formula $R^{10}R^FSiO_{2/2}$; and $T^F$ has the formula $R^FSiO_{3/2}$; where $R^F$ has the formula $(R^1O)_a(R^2O)_b(R^3O)_c(R^4)_d(R^5)_eSiR^U$ with $R^U$ a two to forty atom divalent hydrocarbon radical where the subscripts and components are as previously defined. This non-volatile silicone undergoes a slow hydrolysis under most conditions of use whereby the silicone releases a fragrant alcohol upon hydrolysis. This imparts a desirable odor to many different useful compositions such as cosmetics and household products.

The hydrosilylation reaction is conventionally carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

The compositions of the present invention further provide that the fragrance releasing silicone have one or more substituents $R^1$, $R^2_1$, or $R^3$ where each substituent is independently selected whereby one fragrant alcohol resulting from hydrolysis of said silicone is selected from the group consisting of 2-methylbutanol, 3-pentanol, n-pentanol, 2-pentanol, n-hexanol, 2-methylpentanol, 1-decanol, sandela, nonadyl, dimetol, thymol, 1-heptanol, menthol, eugenol, vanillan, o-vanillan, 4-(p-hydroxyphenyl)-2-butanone, syringealdehyde, prenol, cis-3-hexanol, trans-3-hexanol, cis4-heptenol, trans-2-octenol, trans-2-cis-6-nonadienol, geraniol, nerol, ebanol, citronellol, crotyl alcohol, oleyl alcohol, linalool, a-terpineol, b-phenethyl alcohol, cinnamic alcohol, benzyl alcohol, a -methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octen-ol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool and 2-phenoxyethanol.

The fragrance releasing compounds of the present invention are particularly suited to incorporation into personal care products to impart a desirable long lasting fragrance to the products. Suitable uses include but are not limited to deodorants, antiperspirants, skin creams, facial creams, hair care products such as shampoos, mousses, styling gels, protective creams, shaving creams, after shave, cologne, perfume, color cosmetics such as lipsticks, foundations, blushes, makeup, and mascara; and other cosmetic formulations where other silicon containing components have been added and where it is desirable to impart a fragrance. Incorporation of small amounts of the compositions of the present invention into fragrance products such as shaving lotions, colognes, toilet water, and perfumes can impart a desirable long lasting fragrance to these products. Further, the silanes of the present invention may incorporated into other products where it is desirable to mask unpleasant odors with a pleasant fragrance for example household cleaning products such as waxes and polishes, automobile cleaning products such as waxes and polishes, detergents, textile coatings, paints, varnishes and the like subject to the limitation that the silane of the present invention be compatible or capable of being rendered compatible with the product in which it is incorporated.

Experimental

Vinylsilanes 1–2 were prepared by phenethyl alcohol displacement on the corresponding chlorosilanes. Vinylsilane 3 was a mixture of products consisting of 45% diethoxyphenethyloxy units, 39% ethoxydiphenethyloxy units and 8% triphenethyloxy units that were made by equilibration of a 1:1 mixture of triethoxyvinyl silane and phenethyl alcohol. These vinylsilanes were then attached to various hydrogen containing siloxanes to form the compostitions of the present invention. In turn, 1–3 were allowed to react with $M^H D_{25} M^H$, $MD_{20} D^H_3 M$ and 1,1,1,3,5,5,5-heptamethyltrisiloxane to give polymers 4–9 and siloxanes 10–12 shown below.

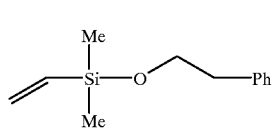

1

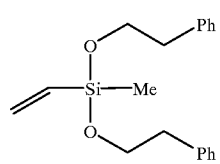

2

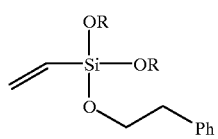

3

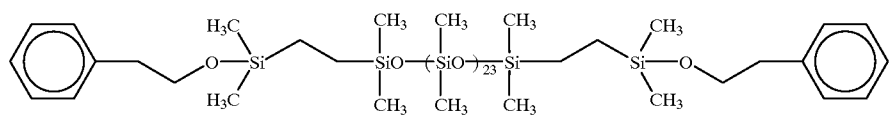

4

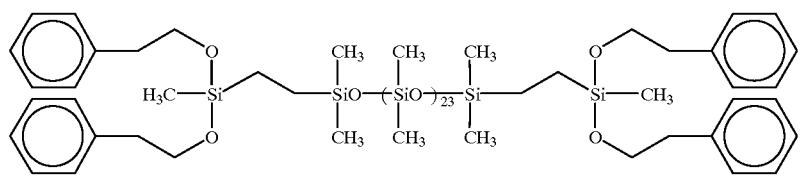

5

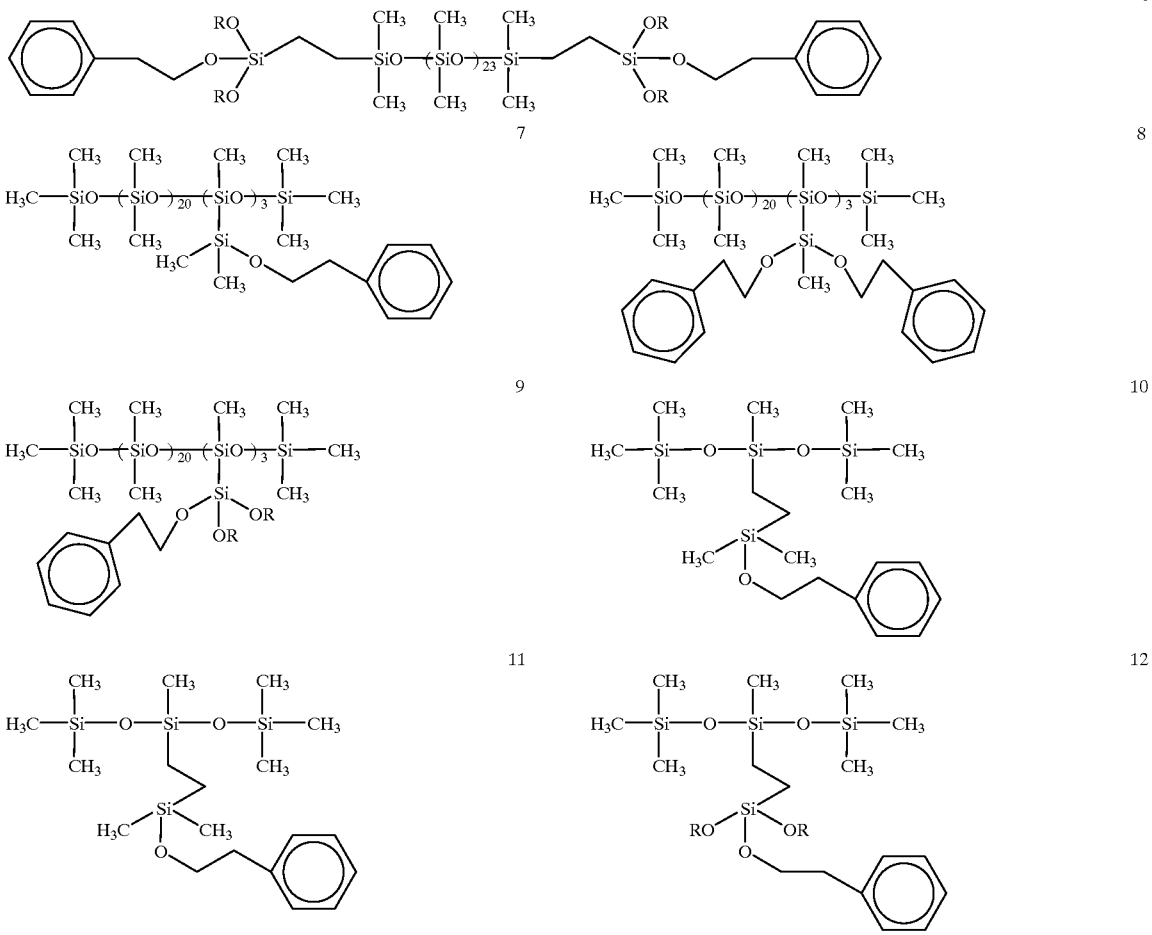

Hydrolysis Experiments

Siloxane 10 was treated with a dilute base solution of NaOH and water and the release of phenethyl alcohol, relative to an internal standard, was monitored by gas chromatography (GC). Table 1 shows that it took about 20 h for 50% of the fragrance to be released. In a similar manner, siloxane 11 and polymers 4 and 5 were treated with aqueous base to effect the catalytic release of the fragrant alcohol. FIG. 1 shows that there was a much more rapid release of the alcohols from materials that possessed two alkoxy groups on a silicon. Compare 10 vs 11 and 4 vs 5.

Polymers 7–9 were also hydrolyzed with dilute base in a similar manner. Table 2 shows the polymer 8, with two phenethyloxy groups hydrolyzed fastest under these conditions and polymers 7 and 9 exhibited slower rates of hydrolysis and had only about 50% of the alcohol released.

TABLE 1

Hydrolysis of Siloxanes 10–11 and Polymers 4–5.

| Siloxane 10 | | Siloxane 11 | | Polymer 4 | | Polymer 5 | |
|---|---|---|---|---|---|---|---|
| Time, hrs. | % Release | Time, hrs. | % Release | Time, hrs. | % Release | Time, hrs. | % Release |
| 0.0 | 0.0 | 1.5 | 22.4 | 3.3 | 12.0 | 0.7 | 0.0 |
| 2.38 | 4.6 | 3.1 | 42.5 | 21.0 | 37.1 | 3.3 | 56.4 |
| 4.5 | 6.6 | 18.2 | 77.6 | 46.0 | 47.8 | 19.9 | 92.0 |
| 21.2 | 52.5 | 42.3 | 88.7 | 141.8 | 51.0 | 27.0 | 92.9 |
| 46.0 | 55.1 | 72.0 | 88.1 | | | 44.0 | 89.5 |
| 165 | 53.6 | 140.9 | 99.6 | | | 97.3 | 94.0 |

TABLE 2

Hydrolysis of Polymers 7–9.

| Polymer 7 | | Polymer 8 | | Polymer 9 | |
|---|---|---|---|---|---|
| Time, hrs. | % Release | Time, hrs. | % Release | Time, hrs. | % Release |
| 0.5 | 8.5 | 0.1 | 7.8 | 0.1 | 10.8 |
| 4.4 | 16.3 | 3.8 | 41.5 | 3.6 | 24.8 |
| 21.0 | 28.3 | 21.0 | 78.0 | 21.1 | 29.5 |
| 45.5 | 40.3 | 45.4 | 96.7 | 45.5 | 33.0 |
| 45.8 | 43.4 | 75.6 | 100.0 | 75.5 | 38.2 |
| 93.3 | 45.2 | 92.8 | 100.0 | 92.6 | 40.8 |

Preparation of Dimethylvinylphenethyloxysilane, 1

Dimethylvinylchlorosilane (150 mL, 1.099 moles) was added to a stirred solution of phenethyl alcohol (124.5 mL, 1.042 moles), triethylamine (TEA, 155 mL, 1.112 moles) and toluene (300 mL) over 1.5 h. After addition, the reaction was heated to 65° C. for 0.5 h then cooled to room temperature, filtered, the filter cake washed with toluene (200 mL), the filtrate concentrated in vacuo and then vacuum distilled (81–85° C./4 mm Hg) to give product (180.5 g, 84%).

Bis(phenethyloxy)methylvinylsilane, 2

Dichloromethylvinylsilane (80 g, 0.567 moles) was added to a stirred solution of phenethyl alcohol (140 g, 114 moles), triethylamine (TEA, 121 g, 1.2 moles) and Isopar C (700 mL) over one hour during which time the reaction mixture was heated to 70° C. After an additional one hour, the reaction was cooled to room temperature, filtered, concentrated in vacuo and then stripped under high vacuum distilled (110° C./4 mm Hg) to give product (1.66 g, 94%).

Phenethyloxydiethoxymethylvinylsilane, 3

Triethoxyvinylsilane (200 g, 1.05 moles), phenethyl alcohol (128 g, 1.05 moles) and Filtrol-20(5 g) were added together and heated to 90° C. Ethanol (EtOH) was distilled off as it formed and the reaction was stopped when most of the phenethyl alcohol had been consumed. The reaction mixture was then stripped at 90° C./4 mm Hg to give a mixture of products which had the following distribution: 45% 3, in which both OR=OEt, 39% 3, in which one OR=OEt and one OR=phenethyloxy, and 8% 3 in which both OR=phenethyloxy.

Terminally Substituted Polymer 4

Polymer $M^H D_{25} M^H$ (80 g, 0.044 moles) was added slowly to a solution of vinylsilane 1 (18.2 g, 0.088 moles) and platinum catalyst (10 mg). When addition was complete the temperature was raised to 80° C. for 2 h then cooled, filtered through Celite to give 90.6 g of a clear colorless liquid.

Terminally Substituted Polymer 5

Polymer $M^H D_{25} M^H$ (60 g, 0.033 moles) was added slowly to a solution of vinylsilane 2 (20.6 g, 0.066 moles) and platinum catalyst (10 mg) at 60° C. When addition was complete the temperature was kept at 60° C. for 4 h the raised to 80° C. for 1 h then cooled and filtered through Celite to give 68.0 g product.

Terminally Substituted Polymer 6

A solution of vinylsilane 3 (20.6 g, 0.066 moles) and platinum catalyst (8 mg) was slowly added to hydride polymer $M^H D_{25} M^H$ at 80° C. When addition was complete the temperature was kept at 80° C. for 8 h then cooled, stripped at high vacuum (130° C./4 mm Hg) and filtered through Celite to give 76.9 g product.

Graft Copolymer 7

Polymer $MD_{20} D^H_3 M$ (80 g, 0.044 moles) was added slowly to a solution of vinylsilane 1 (27.2 g, 0.132 moles) and platinum catalyst (10 mg) at 60° C. When addition was complete the reaction was allowed to react for an additional 2 h then cooled and filtered through Celite to give a clear colorless liquid (98.8 g).

Graft Copolymer 8

Polymer $MD_{20} D^H_3 M$ (100 g, 0.055 moles) was added slowly to a solution of vinylsilane 2 (51.5 g, 0.165 moles) and platinum catalyst (10 mg) at 60° C. During addition the temperature was raised to 90° C. When addition was complete the reaction was allowed to react for an additional 4 h then more catalyst was added (10 mg), heated 5 more hours, another aliquot of catalyst added (10 mg) and additional heating for 7 h. The mixture was then stripped under high vacuum (90° C./4 mm Hg) and filtered through Celite to give 133.3 g product.

Graft Copolymer 9 to a solution of vinylsilane 3 (30.9 g, 0.099 moles) and platinum catalyst (10 mg) was added slowly to polymer $MD_{20} D^H_3 M$ (60 g, 0.033 moles) at 90° C. and allowed to react for 8 h. Two additional aliquots of catalyst (10 mg each) were added over 16 additional hours of heating. The mixture was then stripped under high vacuum (100° C./4 mm Hg) and filtered through Celite to give 75.0 g product.

Siloxane 10

Heptamethyltrisiloxane (40 g, 0.18 moles) was added slowly to a solution of vinylsilane 1 (37 g, 0.18 moles) and platinum catalyst (6 mg) at 60° C. When addition was complete the reaction was allowed to react for an additional 1 h then distilled (~150° C. /4 mm Hg) to give 53.4 g product.

Siloxane 11

Heptamethyltrisiloxane (20 g, 0.09 moles) was added slowly to a solution of vinylsilane 2 (28.1 g, 0.09 moles) and platinum catalyst (6 mg) at 60° C. When addition was complete the reaction was allowed to react for an additional 0.5 h at 80° C. then cooled and filtered to give 43.0 g product.

Siloxane 12

Heptamethyltrisiloxane (40 g, 0.18 moles) was added slowly to a solution of vinylsilane 3 (56.1 g, 0.18 moles) and platinum catalyst (10 mg) at 70° C. When addition was complete the reaction was allowed to react for an additional 12 h at 90° C. with one-additional catalyst (10 mg) addition. The mixture was then cooled stripped under full vacuum (100° C./4 mm Hg) and filtered to give 89.2 g product.

Hydrolysis of Siloxane 10

Siloxane 10 (216 mg, 0.505 mmol) and bibenzyl (68.3 mg, 0.375 mmol) were dissolved in THF (2.0 g) and then treated with 1 wt % NaOH in water (100 mL). Aliquots were removed at timed intervals for GC analysis.

Hydrolysis of Siloxane 11

Siloxane 11 (117.5 mg, 0.220 mmol) and bibenzyl (33.1 mg, 0.182 mmol) were dissolved in THF (2.0 g) and then treated with 1 wt % NaOH in water (100 mL). Aliquots were removed at timed intervals for GC analysis.

Hydrolysis of Polymer 4

Polymer 4 (206.4 mg, 0.092 mmol) and bibenzyl (25.8 mg, 0.141 mmol) were dissolved in THF (2.0 g) and then treated with 1 wt % NaOH in water (40 mL). Aliquots were removed at timed intervals for GC analysis.

Hydrolysis of Polymer 5

Polymer 5 (211.6 mg, 0.086 mmol) and bibenzyl (50.6 mg, 0.278 mmol) were dissolved in THF (2.0 g) and then treated with 1 wt % NaOH in water (80 mL). Aliquots were removed at timed intervals for GC analysis.

Hydrolysis of Polymer 7

Polymer 7 (1368.9 mg, 0.083 mmol) and bibenzyl (50.2 mg, 0.275 mmol) were dissolved in THF (2.0 g) and then treated with 1 wt % NaOH in water (55 mL). Aliquots were removed at timed intervals for GC analysis.

Hydrolysis of Polymer 8

Polymer 8 (187.8 mg, 0.068 mmol) and bibenzyl (59.3 mg, 0.325 mmol) were dissolved in THF (2.0 g) and then treated with 1 wt % NaOH in water (90 mL). Aliquots were removed at timed intervals for GC analysis.

Hydrolysis of Polymer 9

Polymer 9 (117.1 mg, 0.042 mmol) and bibenzyl (59.1 mg, 0.324 mmol) were dissolved in THF (2.0 g) and then treated with 1 wt % NaOH in water (45 mL). Aliquots were removed at timed intervals for GC analysis.

Having described the invention that which is claimed is:

1. A sustained release composition comprising a fragrance releasing siloxane having the formula:

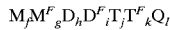

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7, R^8, R^9, R^{10}, R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1O)_a(R^2O)_b(R^3O)_c(R^4O)_d(R^5)_eSiR^U$ with $R^U$ a two to forty atom divalent hydrocarbon radical where $R^1O$, $R^2O$ and $R^3O$ are each independently fragrant alkoxide moieties, derived from the alcohols $R^1OH$, $R^2OH$ and $R^3OH$ wherein $R^1OH$, $R^2OH$ and $R^3OH$ are independently fragrant alcohols with $R^4$ and $R^5$ selected from the group consisting of monovalent hydrocarbon radicals having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3.

2. The fragrance releasing siloxane of claim 1 wherein the subscript a has a value of 2.

3. The fragrance releasing siloxane of claim 1 wherein the subscript a has a value of 3.

4. The fragrance releasing siloxane of claim 1 where the subscript l is 0.

5. The fragrance releasing siloxane of claim 4 where the subscript k is 0.

6. The fragrance releasing siloxane of claim 5 where the subscript j is 0.

7. The fragrance releasing siloxane of claim 6 where the subscript i is 0.

8. The fragrance releasing siloxane of claim 7 where the subscript j is 0.

9. The fragrance releasing siloxane of claim 7 where $R^1$, $R^2$ and $R^3$ are derived from the group of fragrant alcohols consisting of 2-methylbutanol, 3-pentanol, n-pentanol, 2-pentanol, n-hexanol, 2-methylpentanol, 1-decanol, sandela, nonadyl, dimetol, thymol, 1-heptanol, menthol, eugenol, vanillan, o-vanillan, 4-(p-hydroxyphenyl)-2-butanone, syringealdehyde, prenol, cis-3-hexanol, trans-3-hexanol, cis4-heptenol, trans-2-octenol, trans-2-cis-6-nonadienol, geraniol, nerol, ebanol, citronellol, crotyl alcohol, oleyl alcohol, linalool, a-terpineol, b-phenethyl alcohol, cinnamic alcohol, benzyl alcohol, a-methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octen-ol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool and 2-phenoxyethanol.

10. A cosmetic composition selected from the group consisting of deodorants, antiperspirants, skin creams, facial creams, hair care products shampoos, mousses, styling gels, protective creams, shaving creams, after shave, cologne, perfume, lipsticks, foundations, blushes, makeup, and mascara; and other cosmetic formulations where other silicon containing components have been added comprising the fragrance releasing siloxane of claim 1.

* * * * *